United States Patent [19]

Oshida et al.

[11] 4,456,553

[45] Jun. 26, 1984

[54] VITAMIN D3 DERIVATIVES, PROCESS FOR PREPARATION THEREOF, AND ANTIGENS COMPRISING SAID DERIVATIVES TO BE USED FOR PREPARATION OF ANTIBODIES FOR IMMUNOCHEMICAL ASSAY AND ANTIBODIES PREPARED THEREFROM

[75] Inventors: Jun-ichi Oshida, Yamaguchi; Osamu Nishikawa, Tokyo; Hideki Tsuruta, Yamaguchi; Toru Takeshita, Tokyo; Itaru Yamamoto, Okayama; Kenji Ishimaru, Yamaguchi, all of Japan

[73] Assignee: Teijin Limited, Osaka, Japan

[21] Appl. No.: 495,877

[22] Filed: May 18, 1983

Related U.S. Application Data

[63] Continuation-in-part of Ser. No. 376,055, May 7, 1982, abandoned.

[51] Int. Cl.$^3$ .................................................. C07J 9/00
[52] U.S. Cl. ............................. 260/397.2; 260/112 R; 424/88
[58] Field of Search ..................................... 260/397.2

[56] References Cited

U.S. PATENT DOCUMENTS 4,263,215  4/1981  Hesse et al. ................. 260/397.20 R
4,329,295  5/1982  Chorvat ....................... 260/397.20 R

*Primary Examiner*—John Kight, III
*Assistant Examiner*—Garnette D. Draper
*Attorney, Agent, or Firm*—Sughrue, Mion, Zinn, Macpeak & Seas

[57] ABSTRACT

The present invention relates to novel vitamin $D_3$ derivatives which have a carboxyl group or its ester group at the 22-position, processes for the preparation thereof, and antigens, which comprise said vitamin $D_3$ derivative and an immunogenic carrier material, to be used for the preparation of antibodies for enzymeimmunoassay or radioimmunoassay and antibodies obtained therefrom.

The determination of such activated vitamin $D_3$ compounds as 25-hydroxy vitamin $D_3$, 24, 25-dihydroxy vitamin $D_3$, etc. can be made satisfactorily according to the present invention.

6 Claims, No Drawings

VITAMIN D₃ DERIVATIVES, PROCESS FOR PREPARATION THEREOF, AND ANTIGENS COMPRISING SAID DERIVATIVES TO BE USED FOR PREPARATION OF ANTIBODIES FOR IMMUNOCHEMICAL ASSAY AND ANTIBODIES PREPARED THEREFROM

CROSS-REFERENCE OF RELATED APPLICATION

This is a continuation-in-part application of U.S. patent application Ser. No. 376,055, filed May 7, 1982, now abandoned.

BACKGROUND OF THE INVENTION

1. Field of the Invention

The present invention relates to novel vitamin $D_3$ derivatives, processes for the preparation thereof, and antigens comprising said derivatives for the preparation of antibodies for immunochemical assay and antibodies prepared therefrom.

More particularly, the present invention relates to novel vitamin $D_3$ derivatives which have a carboxyl group or its ester group at the 22-position, processes for the preparation thereof, and antigens, which comprise said vitamin $D_3$ derivative and an immunogenic carrier material for the preparation of antibodies for enzymeimmunoassay or radioimmunoassay and antibodies obtained by inoculating a host animal with said antigen for an enzymeimmunoassay or radioimmunoassay.

2. Description of the Prior Art

It has been established that vitamin $D_3$ is metabolized in the kidney or liver into 25-hydroxy-vitamin $D_3$, 1α,25-dihydroxyvitamin $D_3$, 24,25-dihyroxyvitamin $D_3$. Such metabolites as 25-hydroxyvitamin $D_3$, 1α,25-dihydroxyvitamin $D_3$, and such activated vitamin $D_3$ compounds as 1α-hydroxyvitamin $D_3$, 1α,24-dihydroxyvitamin $D_3$, are used clinically as a remedy for osteoporosis, osteomalacia, and their development is now taking place. However, these remedies are clinically administered in very small dosages in general and a single dose is in the range of several hundreds ng to several dozens μg.

On the other hand, the pharmacological action of a remedy has the interrelationship with its concentration in the serum or tissue, and the determination of the concentration of the remedy is clinically very important in the case of human beings.

As a method for the determination of the concentration of an activated vitamin $D_3$ compound, a radioreceptor assay, wherein 1α,25-dihydroxyvitamin $D_3$ receptor is used, has hitherto been known (Biochemistry, 13, 4091 (1974)). However, faults are found with this assay in that it demands a slow, laborious process to perform, requires large quantities of serum, and above all obtained results are not always satisfactorily accurate.

As for another assays, Japanese patent application Laid-Open No. 47653/80 discloses a radioimmunoassay wherein 1α-hydroxyvitamin $D_3$3-hemisuccinate or 1α,25-dihydroxyvitamin $D_3$ 3-hemisuccinate is used as a hapten. Also Japanese patent application Laid-Open No. 87344/78 discloses a radioimmunoassay wherein 1α,25-dihydroxyvitamin $D_3$ 25-hemisuccinate is used as a hapten.

In these radioimmunoassays, antigens for use in the assays are those obtained by bonding a carrier protein to a hapten by means of a carboxyl group in the substituent group at the 25-position or the 3-position of said hapten.

It is generally known that the antibody (antihapten antibody) of an antigen for assay use recognizes the chemical structure on the hapten apart from the place of its binding site to the carrier protein.

Accordingly, there is a strong probability that those antihapten antibodies obtained by use of such haptens as mentioned in the above cited patent come to have less competency to recognize the structure of the hapten at the 25-position, 1α-position, or 24-position.

SUMMARY OF THE INVENTION

Through intensive researches, we have synthesized novel vitamin $D_3$ derivatives which have a carboxyl group or its ester group at the 22-position and found that these vitamin $D_3$ derivatives are very useful as a hapten for an enzymeimmunoassay or radioimmunoassay which is preferably adopted for the determination of the concentration of an activated vitamin $D_3$ compound having a hydroxyl group at the 1α-position, 24-position, or 25-position, thus achieving the present invention.

The present invention is concerned with:

Vitamin $D_3$ derivatives expressed by the following formula (I):

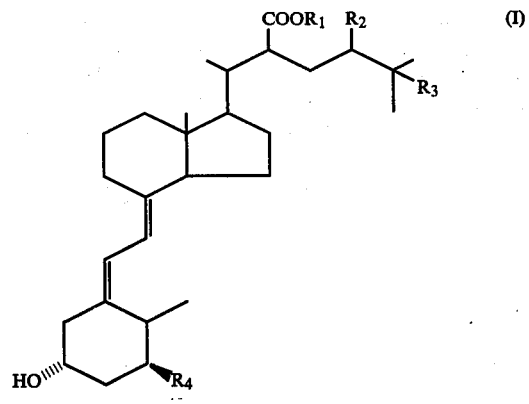

wherein $R_1$ is a hydrogen atom or an alkyl group with 1 to 6 carbon atoms having a carboxyl group or amino group; $R_2$, $R_3$, and $R_4$ independently indicate a hydrogen atom or hydroxyl group Processes for the preparation of a vitamin $D_3$ derivative expressed by the abovementioned formula (I), which processes are characterized by subjecting a cholesta-5,7-diene derivative expressed by the following formula (II)

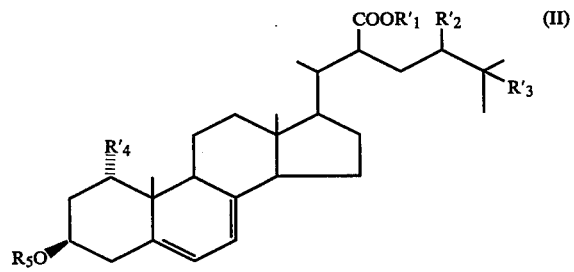

wherein $R'_1$ is a hydrogen atom, alkyl group with 1 to 6 carbon atoms, alkyl group with 1 to 6 carbon atoms having a carboxyl group or amino group, or alkyl group with 1 to 6 carbon atoms having a protected carboxyl group or protected amino group; $R'_2$, $R'_3$, and $R'_4$ independently indicate a hydrogen atom, hydroxyl group, or protected hydroxyl group; and $R_5$ is a hydrogen atom or protecting group, to the thermal isomerization after ultraviolet irradiation in an inert organic medium, followed by deprotection, if necessary; antigens, which are prepared by covalently bonding said vitamin $D_3$ derivative expressed by formula (I) through its carboxyl group or amino group to an immunogenic carrier material for the preparation of an antibody for immunochemical assay; and antibodies, which are induced by inoculating a host animal with said antigen prepared by covalently bonding the abovementioned vitamin $D_3$ derivative expressed by formula (I) through its carboxyl group or amino group to an immunogenic carrier material for immunochemical assay.

DESCRIPTION OF THE PREFERRED EMBODIMENTS

A novel vitamin $D_3$ derivative offered in the present invention is a compound expressed by the aforementioned formula (I) and has a characteristic chemical structure which has a carboxyl group or its ester group at the 22-position.

In the aforementioned formula (I), $R_1$ indicates a hydrogen atom or an alkyl group with 1 to 6 carbon atoms having a carboxyl group or amino group. As alkyl groups with 1 to 6 carbon atoms having a carboxyl group or amino group, there may be exemplified alkyl groups with 1 to 6 carbon atoms having a carboxyl group such as carboxymethyl group, 2-carboxyethyl group, 3-carboxypropyl group, 4-carboxybutyl group, 5-carboxyheptyl group, 6-carboxyhexyl group, etc. and alkyl groups with 1 to 6 carbon atoms having an amino groups such as aminomethyl group, 2-aminoethyl group, 3-aminopropyl group, 4-aminobutyl group, 5-aminoheptyl group, 6-aminohexyl group. Of these mentioned above, a hydrogen atom is especially preferable as $R_1$.

Also in the aforementioned formula (I), $R_2$, $R_3$, and $R_4$ independently indicate a hydrogen atom or hydroxyl group. These vitamin $D_3$ derivatives whose $R_2$ and $R_3$ are both hydroxyl groups are especially preferable as haptens for assaying activated vitamin $D_3$ such as 24,25-dihydoxyvitamin $D_3$.

Concrete examples of vitamin $D_3$ derivatives expressed by the aforementioned formula (I) include the following:

(1) 22-carboxy-24,25-dihydroxycholecalciferol,
(2) 22-carboxy-1α,24,25-trihydroxycholecalciferol,
(3) 22-carboxy-25-hydroxycholecalciferol,
(4) 22-carboxy-1α,25-dihydroxycholecalciferol,
(5) 22-carboxy-1α,24-dihydroxycholecalciferol,
(6) 22-carboxy-1α-hydroxycholecalciferol,
(7) 22-(2-carboxyethoxycarbonyl)-24,25-dihydroxycholecalciferol,
(8) 22-(2-carboxyethoxycarbonyl)-1α,24,25-trihydroxycholecalciferol,
(9) 22-(2-carboxyethoxycarboxyl)-1α,25-dihydroxycholecalciferol,
(10) 22-(2-carboxyethoxycarbonyl)-25-hydroxy cholecalciferol,
(11) 22-(2-carboxyethoxycarbonyl)-1α-hydroxycholecalciferol,
(12) 22-(2-aminoethoxycarbonyl)-24,25-dihydroxycholecalciferol,
(13) 22-(2-aminoethoxycarbonyl)-1α,25-dihydroxycholecalciferol,
(14) 22-(2-aminoethoxycarbonyl)-1α-hydroxycholecalciferol.

The abovementioned vitamin $D_3$ derivatives of the present invention are prepared as follows. Their preparation is carried out by subjecting a cholesta-5,7-diene derivative expressed by the following formula (II)

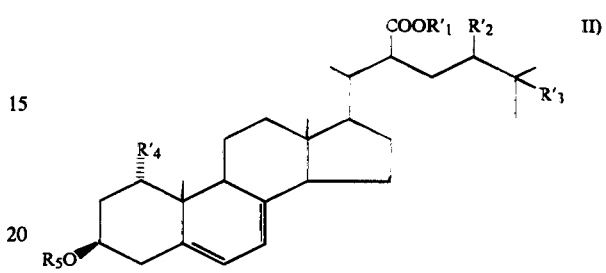

wherein definitions of $R'_1$, $R'_2$, $R'_3$, $R'_4$, and $R_5$ are the same as those given earlier, to the thermal isomerization after ultraviolet irradiation in an inert organic medium, followed by deprotection, if necessary.

The material compound, or said cholesta-5,7-diene derivative expressed by formula (II), can be prepared from its corresponding cholest-5-ene derivative by allylic bromination followed by debromination.

In addition, the cholest-5-ene derivative, i.e., the C-22-carboxyl-$\Delta^5$-cholestene can be prepared by the following reaction scheme:

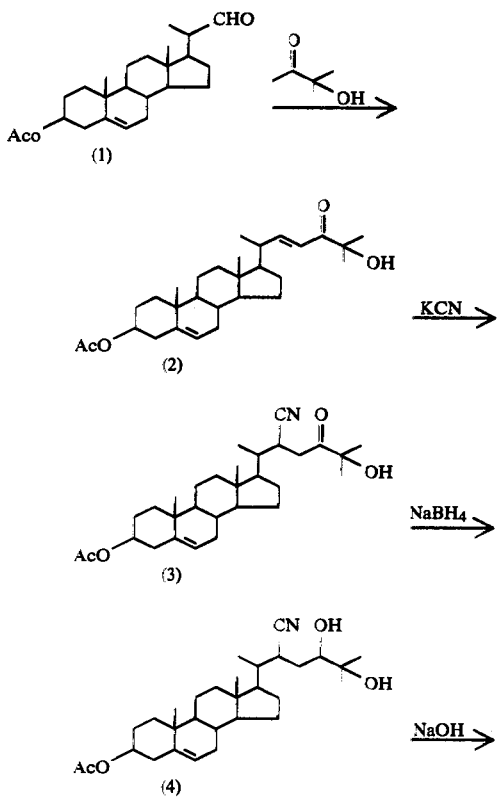

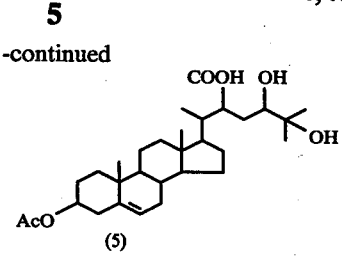

(5)

Compound (2) is prepared by the reaction of compound (1), which is described in *J. Amer. Chem. Soc.*, Vol. 69, Page 1957 (1947) and *J. Amer. Chem. Soc.*, Vol. 70, Page 2953 (1948), with 3-methyl-3-hydroxylbutane-2-one. Next, compound (2) can be readily converted to compound (3) by reacting compound (2) with potassium cyanide. The C-22-carboxyl-$\Delta^5$-cholestene, i.e., compound (5) is prepared by the reduction of compound (3) with sodium borohydride followed by hydrolysis with sodium hydroxide.

The above synthesis is described in detail in Japanese patent application Nos. 55-155806 and 55-155808 which correspond to Japanese Laid-open Application Nos. 57-80400 and 57-80399.

In the abovementioned formula (II), $R'_1$ indicates a hydrogen atom, alkyl group with 1 to 6 carbon atoms, alkyl group with 1 to 6 carbon atoms having a carboxyl group or amino group, or alkyl group with 1 to 6 carbon atoms having a protected carboxyl group or protected amino group.

As alkyl groups with 1 to 6 carbon atoms, there may be exemplified a methyl group, ethyl group, propyl group, butyl group, t-butyl group, heptyl group, hexyl group. As alkyl groups with 1 to 6 carbon atoms having a carboxyl group or amino group, there may be mentioned those given in $R_1$ in the aforementioned formula (I). As alkyl groups with 1 to 6 carbon atoms having a protected carboxyl group or protected amino group, the following ones may be exemplified. Those alkyl groups with 1 to 6 carbon atoms having a carboxyl group cited as examples of $R_1$ of the aforementioned formula (I), wherein said carboxyl group is a group which forms an ester bond, may be mentioned including, for instance, a methoxycarbonylmethyl group, ethoxycarbonylmethyl group, butoxycarbonylmethyl group, 2-methoxycarbonylethyl group, 2-ethoxycarbonylethyl group, 2-butoxycarbonylethyl group. As alkyl groups with 1 to 6 carbon atoms having a protected amino group, those alkyl groups with 1 to 6 carbon atoms having an amino group cited as examples of $R_1$ of the aforementioned formula (I), wherein said amino group is a group which forms an amide bond, may be mentioned including, for instance, an acetylaminomethyl group, 2-acetylaminoethyl group, 4-acetylaminobutyl group.

In the aforementioned formula (II), $R'_2$, $R'_3$, and $R'_4$ independently indicate a hydrogen atom, hydroxyl group, or protected hydroxyl group and $R_5$ represents a hydrogen atom or protecting group. As protecting groups in the case where $R'_2$, $R'_3$, and $R'_4$ are protected hydroxyl groups or where $R_5$ is a protecting group, there may be mentioned, for instance, aliphatic or aromatic carboxylic acid residues with 1 to 12 carbon atoms such as an acetyl group, propanoyl group, butanoyl group, pivaloyl group, pentanoyl group, cyclohexanoyl group, chloroacetyl group, bromoacetyl group, benzoyl group, p-bromobenzoyl group, p-nitrobenzoyl group, ethylbenzoyl group, toluyl group or their nitro-, halogeno-, or alkoxy-substituted derivatives; or trialkylsilyl groups such as a trimethylsilyl group, dimethyl-t-butylsilyl group; or 2-cyclic ether groups such as a 2-tetrahydropyranyl group, 2-tetrahydrofuranyl group. Of these protecting groups, an acetyl group, propanoyl group, butanoyl group, pivaloyl group, pentanoyl group, cyclohexanoyl group and benzoyl group are preferable.

These cholesta-5,7-diene derivatives expressed by the aforementioned formula (II) are thermally isomerized after ultraviolet irradiation in an inert organic medium. As ultraviolet rays to be used for ultraviolet irradiation, those having wavelengths of about 200 to 360 nm, preferably those having wavelengths of 260 to 310 nm, are used.

The ultraviolet irradiation reaction is carried out in an inert organic medium. As inert organic mediums, hydrocarbon or halogenated hydrocarbon such as hexane, heptane, benzene, toluene, xylene, chlorobenzene, and carbontetrachloride; ethers such as diethyl ether, tetrahydrofuran, and dioxane; or alcohols such as methanol, ethanol, and propanol are used as desirable ones.

In the ultraviolet irradiation reaction, reaction temperature has not much significance; however, the reaction is usually carried out at $-20°$ C. to 120° C., especially in the range of $-10°$ C. to 50° C.

In this reaction, C—C bond cleavage is caused at the $-9-$ and 10-positions of said cholesta-5,7-diene derivative to convert it into a previtamin $D_3$ derivative. Thus obtained previtamin $D_3$ derivative is then isomerized by thermal energy into a vitamin $D_3$ derivative. This isomerization reaction is an equilibrium reaction between the previtamin $D_3$ derivative and the vitamin $D_3$ derivative and their equilibrium values differ depending upon the reaction temperature.

In the present invention, the isomerization reaction is conducted at 20° to 120° C., preferably at 40° to 100° C. This isomerization reaction can be satisfactorily conducted in the inert organic medium in which said ultraviolet irradiation has been carried out.

Therefore, in the case where said ultraviolet irradiation, by which previtamin $D_3$ derivative is prepared, is conducted at 40° C., for instance, previtamin $D_3$ derivative, which is formed as C—C bond is being cleaved at the 9- and 10-positions of cholesta-5,7-diene derivative, gradually isomerizes into vitamin $D_3$ derivative in the same reaction system coincidently. The isomerization reaction by thermal energy proposed in the present invention does not necessarily mean the heating of the reaction system as clearly understood from what mentioned above.

Said vitamin $D_3$ derivative expressed by formula (I) or its derivative having protected hydroxyl group, protected carboxyl group, or protected amino group is thus prepared. In case the hydroxyl group, carboxyl group or amino group is protected, said isomerization reaction must be followed by the removal of the protecting groups. This deprotection reaction is itself a publicly known reaction and may be carried out, for instance, when the protecting group forms an acyl group, by treating with an alkaline solution in lower aliphatic alcohol such as methanol and ethanol or with metal hydride such as $LiAlH_4$ in ether. The reaction temperature may be in the range of $-10°$ C. to 50° C. In case the protecting group is bonded to an oxygen atom of a hydroxyl group to form an ether group, it can be easily removed by reductive treatment or by treatment with acid or alkali.

The above is the way by which said vitamin $D_3$ derivative expressed by formula (I) is obtained.

In the case where $R_1$ of said vitamin $D_3$ derivative expressed by formula (I) is an alkyl group with 1 to 6 carbon atoms having a carboxyl group or amino group, the vitamin $D_3$ derivative can also be obtained by the following procedure. It can be prepared by subjecting vitamin $D_3$ derivative expressed by the aforementioned formula (I) in which $R_1$ is a hydrogen atom and hydroxy acid with 1 to 6 carbon atoms having a carboxyl group such as glycolic acid, lactic acid, $\beta$-hydroxypropionic acid or an amine compound with 1 to 6 carbon atoms having an amino group such as 2-hydroxyethylamine, 3-hydroxybutylamine to the esterification reaction. The isolation and the purification of the obtained vitamin $D_3$ derivative is accomplished by column chromatography, thin-layer chromatography, high-pressure liquid chromatography, recrystallization.

Vitamin $D_3$ derivatives expressed by formula (I) offered by the present invention are novel compounds which find no mention in any literature and have a characteristic chemical structure of having a carboxyl group or its ester group at the 22-position. Such vitamin $D_3$ derivatives are very useful as hapten for enzymeimmunoassay or radioimmunoassay which is desirable for the determination of activated vitamin $D_3$ compound having a hydroxyl group at the 1$\alpha$-, 24-, or 25-position.

When said vitamin $D_3$ derivative expressed by formula (I) is used as hapten for enzymeimmunoassay or radioimmunoassay, said hapten is covalently bonded to an immunogenic carrier material to form an antigen for the preparation of an antihapten antibody. An antibody prepared from the antigen is offered as one of the reagents which make up the assay kit for enzymeimmunoassay or radioimmunoassay.

The present invention offers an antigen which is formed by covalently bonding said vitamin $D_3$ derivative expressed by formula (I) to an immunogenic carrier material through the carboxyl group or amino group of the vitamin $D_3$ derivative for the preparation of an antibody for immunochemical assay, and an antibody which is induced by inoculating a host animal with said antigen for immunochemical assay.

As immunogenic carrier materials for obtaining an antigen by covalent bonding to a vitamin $D_3$ derivative, there may be mentioned proteins, polypeptide, glycoprotein. Examples of suitable proteins include bovine serum albumin (BSA), human serum albumin (HSA), human gamma globulin, methylated bovine serum albumin, rabbit serum albumin, and bovine gamma globulin. As polypeptides, polylysine, poly-L-lysine-polyglutamic acid copolymer may be cited as examples. As examples of glycoproteins, lipopolysaccharide, ficoll, keyholelymphet, hemocyanin may be mentioned. Of them, proteins are preferred and bovine serum albumin and human serum albumin are especially preferred.

The covalent coupling of said vitamin $D_3$ derivative expressed by formula (I) to an immunogenic carrier material is carried out directly or indirectly through a carboxyl group or amino group at the 22-position of the vitamin $D_3$ derivative and a functional group of the immunogenic carrier material. As functional groups of the immunogenic carrier material, an amino group of lysine, carboxyl group or amino group of aspartic acid or glutamic acid, phenolic hydroxyl group in a tyrosine residue, and mercapto group of cysteine, for instance, may be mentioned.

As methods of covalent bonding, there may be mentioned a method in which N-hydroxysuccinimide or alkylchloroformate is reacted with a carboxyl group or amino group of the vitamin $D_3$ derivative to activate the carboxyl group or amino group of the vitamin $D_3$ derivative, followed by covalent bond formation; a method in which a condensing agent such as 1-ethyl-3-(3-dimethylaminopropyl)-carboxyimide hydrochloride, dicyclohexylcarbodiimide, N-ethyl-5-phenylisoxazolium-3'-sulfonate is used; or a method in which both of these methods are used in combination. Especially preferable method is one in which an activating agent such as N-hydroxysuccinimide and a condensing agent such as dicyclohexylcarbodiimide are used together.

An example of preferred embodiments is one in which a solution of, for instance, 22-carboxy-24,25-dihydroxycholecalciferol, N-hydroxysuccinimide, and dicyclohexylcarbodiimide in tetrahydrofuran is left standing at room temperature for some dozen hours to form N-hydroxysuccinimide ester of 22-carboxy-24,25-dihydroxycholecalciferol, which is then reacted with human serum albumin in a buffer solution of phosphoric acid.

It is preferable to keep the number of molecules of vitamin $D_3$ derivative to be bonded to an immunogenic carrier material in the range of 5 to 20 against 1 molecule of the immunogenic carrier material, especially preferable to be kept in the range of 5 to 10.

Thus obtained antigen for the preparation of an antibody for immunochemical assay is inoculated into a host animal to induce the formation of an antibody.

As host animals, warm-blooded animals such as rabbits, rats, cows, sheep may be mentioned. The inoculation of the antigen into a host animal is practised by extrabuccal administration, for instance, by means of hypodermic or intradermal injection. The inoculation of the antigen is usually conducted with the combined use of Freund's complete adjuvent.

The inoculation is conducted by injecting 200 $\mu$g of the same antigen hypodermically or intradermally at an interval of four weeks. During the period of inoculation, the antibody concentration of the blood is determined every ten days and the total blood is withdrawn when the highest titer is obtained. The serum separated from thus obtained blood may be used as antigen without any treatment; however, it is preferable to adjust the antibody concentration by obtaining IgG fractions by means of ammonium sulfate fractionation or gel filtration.

Since respective antibodies thus obtained can recognize activated vitamin $D_3$ having a hydroxyl group at the 1$\alpha$-,24-, or 25-position such as compounds of 1$\alpha$-hydroxy vitamin $D_3$, 25-hydroxy vitamin $D_3$, 1$\alpha$, 25-dihydroxy vitamin $D_3$, and 24,25-dihydroxy vitamin $D_3$, they are useful as antibodies for enzymeimmunoassay or radioimmunoassay.

When such antibodies are used for enzymeimmunoassay, they are used together with an enzyme-labelled antigen as one of the reagents which make up the assay kit.

As enzyme-labelled antigens cited herein, those which can be obtained by covalently coupling said vitamin $D_3$ derivative expressed by formula (I) to such enzymes as $\beta$-D-galactosidase, alkaline phosphatase, glucose oxidase, lipase, peroxidase, preferably such enzymes as $\beta$-D-galactosidase and alkaline phosphatase may be mentioned.

When the antibodies of the present invention are used for radioimmunoassay, they are used together with 24,25-dihydroxy vitamin D₃, 25-hydroxy vitamin D₃, 1α-hydroxy vitamin D₃, and 1α-25-dihydroxyvitamin D₃ which are radiolabelled with $^3$H (tritium) or $^{14}$C as one of the reagents which make up the assay kit. Also said antibodies can be used together with $^{125}$I-Protein A, which is labelled with $^{125}$I, as reagents for radioimmunoassay which is called Sandwich method.

The present invention is illustrated below with reference to the examples:

EXAMPLE 1

(i) Preparation of 22-methoxycarbonyl-3β,24-diacetoxycholesta-5,7-dien-25-ol:

1,3-Dibromo-5,5-dimethylhydantoin (137.7 mg) was added to a refluxing solution of 22-methoxycarbonyl-3β,24-diacetoxycholest-5-en-25-ol (450 mg) in carbon tetrachloride (10 ml), and the mixture was stirred for 15 minutes under a nitrogen atmosphere with an infrared lamp irradiation. The mixture was then cooled and filtered. Evaporation of the filtrate gave a crude product. A solution of the crude product in xylene (12 ml) was added dropwise to a refluxing solution of xylene (7.5 ml) and s-collidine (2.5 ml) and the mixture was refluxed for 20 minutes.

The reaction mixture was extracted twice with ethyl acetate and the organic layer was washed with 1N-HCl, sat. NaHCO₃ solution and brine, then dried over Na₂SO₄. The solvent was evaporated off. Purification of the product by preparative TLC on silica gel developed with benzene-ethylacetate gave 22-methoxy-3β,24-diacetoxycholesta-5,7-diene-25-ol (154 mg, 35%). Its physical properties were as follows:

UV($\lambda_{max}^{EtOH}$): 293, 281, 271 and 262(sh) nm.

High resolution mass spectrum, calculated for $C_{31}H_{46}O_5$ (M$^+$-AcOH), 498.3345, found 498.3358.

(ii) Preparation of 22-methoxycarbonyl-3β,34-diacetoxy-25-hydroxyvitamin D₃:

A solution of 22-methoxycarbonyl-3β,24-diacetoxy-cholesta-5,7-dien-25-ol (100 mg) in deoxygenated benzene (600 ml) was irradiated with a 200 W Hanovia lamp through a Vycor filter at 5° C. for 7.5 minutes while argon was bubbled through the solution. Then the solution was concentrated to about 100 ml under reduced pressure below 30° C. and the concentrated solution was refluxed for 2.5 hours. Evaporation of the solvent gave a crude product. A development of the crude product on a silver nitrate-impregrated silica gel plate with chloroform-methanol as eluent followed by preparative TLC on silica gel with benzene-ethyl acetate as eluent gave 22-methoxycarbonyl-3β,24-diacetoxy-25-hydroxyvitamin D₃ (25.5 mg). Its physical properties were as follows:

UV(EtOH; nm): λmax, 263 ($\epsilon$=15500); λmin, 228 ($\epsilon$=8200).

MS (m/e): 558 (M$^+$), 498, 281, 253, 158, 118.

High resolution mass spectrum, calculated for $C_{33}H_{50}O_7$ 558.3559, found 558.3660.

(iii) Preparation of 22-carboxyl-24,25-dihydroxyvitamin D₃:

A mixture of 22-methoxycarbonyl-3β,24-diacetoxy-25-hydroxyvitamin D₃ (14 mg), 10% KOH-MeOH (2 ml) and tetrahydrofuran (2 ml) was stirred for 2.5 hours at 65° C. under a nitrogen atmosphere. After the addition of acetic acid 10.25 ml), the mixture was extracted with ethyl acetate. The organic phase was washed with brine and dried over Na₂SO₄. The solvent was evaporated off. Purification of the product by preparative TLC on silica gel developed with benzeneethyl acetate afforded 22-carboxyl-24,25-dihydroxyvitamin D₃ (9.8 mg). Its physical properties were as follows:

UV (EtOH; nm): λmax, 263 ($\epsilon$=15700); λmin, 227.5 ($\epsilon$=8300).

MS (m/e): 442 (M$^+$-H₂O), 424, 406, 136, 118.

High resolution mass spectrum, calculated for $C_{28}H_{42}O_2$ (M$^+$-H₂O), 442.3083, found 442.3117.

EXAMPLE 2

Preparation of 22-carboxyl-24,25-dihydroxycholecalciferol-HSA conjugate (i) Preparation of N-hydroxysuccinimide ester of 22-carboxyl-24,25-dihydroxycholecalciferol.

A mixture of 22-carboxyl-24,25-dihydroxycholecalciferol (1.0×10$^{-6}$ mol), N-hydroxysuccinimide (1.5×10$^{-6}$ mol), and dicyclohexylcarbodiimide (DCC, 1.5×10$^{-6}$ mol) in tetrahydrofuran (THF, 900 μl) was stirred for 12 hours at 4° C. in the dark.

The resulting dicyclohexylurea precipitate was eliminated by centrifugation (10000 g×10 min).

The supernatant was evaporated off under reduced pressure, and this N-hydroxysuccinimide ester obtained was dissolved in 200 μl of THF.

(ii) Reaction of N-hydroxysuccinimide ester with HSA.

A mixture of N-hydroxysuccinimide ester in THF (200 μl) and HSA (5 mg) in 0.05M phosphate buffer at pH 7.4 (500 μl)-pyridine (100 μl) was stirred at 4° C. for 12 hours.

200 μl of THF was added to the resulting mixture and then this solution was dialyzed against cold 50% THF/water for 12 hours and further against cold water for 48 hours and lyophilized to give 22-carboxyl-24,25-dihydroxycholecalciferol-HSA conjugate.

EXAMPLE 3

Preparation of anti-22-carboxyl-24,25-dihydroxycholecalciferol-HSA-antibody

Rabbits were immunized with the 22-carboxyl-24,25-dihydroxycholecalciferol-HSA conjugate prepared as described in Example 2, (ii), used as an antigen to obtain its antibody as follows:

Two male rabbits (ca. 2 kg) were primed subcutaneously with 100 μl of antigen solution (22-carboxyl-24,25-dihydroxycholecalciferol-HSA in saline, 200 μg-protein/head) in Freund's Complete Adjuvant (1/1) and boosed subcutaneously with 100 μl of antigen solution (200 μg-protein/head) in Freund's Complete Adjuvant (1/1) 4,8, and 12 weeks later respectively. 10 weeks after the second booster injection, the rabbits were injected intravenously with 100 μl of antigen solution.

An anti-serum usable for radioimmunoassay or enzymeimmunoassay was obtained in this way in about 4 months after the immunization was started.

EXAMPLE 4

Solid phase radioimmunoassay for anti-22-carboxyl-24,25-dihydroxycholecalciferol-HSA antibody with protein A It was examined according to the procedure described hereunder by usé of the undermentioned reagents if the anti-22-carboxyl-24,25-dihydroxycholecalciferol antibody prepared as described in Example 3 can recognize vitamin $D_3$.

Reagents:
$^{125}$I-labeled Protein A (8.32 nCi/ng protein),
Antigen: succinyl Vitamin $D_3$-BSA,
Microtiter plates, "U" bottom, disposable, flexible, nonsterile, Gamma counter,
RIA buffer:
A buffer:
0.05M phosphate buffer pH 7.4, 0.1% $NaN_3$
B buffer:
0.05M phosphate buffer pH 7.4, 1.0% BSA, 0.1% $NaN_3$
C buffer:
0.05M phosphate buffer pH 7.4, 0.1% Tween 20, 0.1% $NaN_3$ Procedure:

(A)
The antigen (succinyl Vitamin $D_3$-BSA) is dissolved in A buffer to make a final concentration of approximately 20 μg/ml protein (2 μg/well (max.), 100 ng/well).
An antigen aliquot (100 μl) or A buffer is placed in the wells and incubated at 37° C. for 1 hour.

(B)
The antigen is aspirated and 0.2 ml of B buffer is added to each well.
Each of the wells is incubated at 37° C. for 1 hour, aspirated and washed three times with cold C buffer and then carefully dried.

(C)
The antibody (100 μl) is then added to each well and incubated at 4° C. for 12 hours. The wells are aspirated, washed three times with cold C buffer and dried.

(D)
A 100 μl aliquot of 250 ng/ml solution of $^{125}$I-labeled Protein A (approximately 25 ng/well) is added to each well.
This is incubated at room temperature for 22 to 24 hours.

(E) The wells are aspirated, washed three times in cold C buffer, dried, cut with scissors, placed in counting tubes, and counted in a γ-counter.

It was confirmed that $^{125}$I-protein A was coupled to vitamin $D_3$-antibody conjugate and that the anti-22-carboxy-24,25-dihydroxycholecalciferol-HSA-antibody could therefore recognize vitamin $D_3$ from the fact that the count obtained from the determination made with a γ-counter corresponded to the prescribed count.

(ii) A calibration curve was drawn for the radioimmunoassay range with $^{125}$I-protein A according to the following procedure with the use of the reagents mentioned in the preceding (i) and 1α,25-dihydroxy vitamin $D_3$ as compound specimen.

Procedure:

(A)
The antigen (succinyl Vitamin $D_3$-BSA) is dissolved in A buffer. An antigen aliquot (100 μl) or A buffer is placed in the wells and incubated at 37° C. for 1 hour.

(B)
The antigen is aspirated and 0.2 ml of B buffer is added to each well. Each well is incubated at 37° C. for 1 hour, aspirated, washed three times with cold C buffer, again with A buffer, and then carefully dried.

(C)
The antibody solution/A buffer (100 μl) and 10 μl of 1,25-dihydroxy vitamin $D_3$ solution are added to each well and incubated at 4° C. for 12 hours. (The anti-serum dilutions of 1:1600–1:9600 usually fall in the range of the standard curve.)
The wells are aspirated, washed three times with C buffer, again with A buffer, and then dried.

(D)
A 100 μl of 250 ng/ml solution of $^{125}$I-Protein A (approximately 25 ng/well) is added to each well. This is incubated at room temperature for 22 to 24 hours.

(E)
The wells are aspirated, washed three times in cold C buffer, dried, cut with scissors, placed in different counting tubes and counted in a γ-counter.

A calibration curve was drawn by determining the respective ratios ($^{125}$I-radioactivity (B/Bo %) of γ-counts between the two kinds of solutions, one without addition of 1α,25-dihydroxy vitamin $D_3$ and the other with addition of 1α,25-dihydroxy vitamin $D_3$, following the above procedure with the concentration 1α,25-dihydroxyvitamin $D_3$ changed variously.

It was made clear from this calibration curve that the determination of 1,25-dihydroxyvitamin $D_3$ in the range of 10 of to 1 p (mol/well) was made possible satisfactorily by use of the antibody diluted 9600 times and the antigen diluted $10^{13}$ times.

What we claim is:

1. A vitamin $D_3$ derivative expressed by the following formula (I)

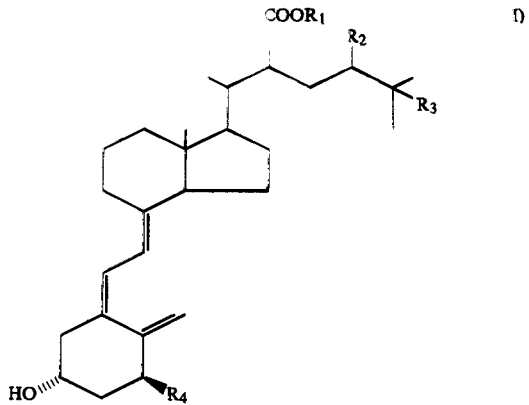

wherein $R_1$ is a hydrogen atom or an alkyl group with 1 to 6 carbon atoms having a carboxyl group or amino group; $R_2$, $R_3$, and $R_4$ independently indicate a hydrogen atom or hydroxyl group.

2. A vitamin $D_3$ derivative according to claim 1, wherein $R_1$ is a hydrogen atom in the abovementioned formula (I).

3. A vitamin $D_3$ derivative according to claim 1, wherein both $R_2$ and $R_3$ are hydroxyl group in said formula (I).

4. A process for the preparation of a vitamin $D_3$ derivative expressed by the following formula (I)

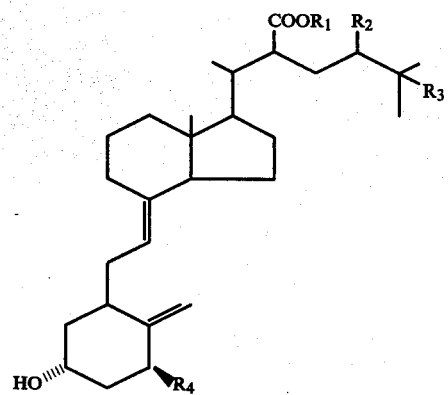

wherein the definitions of $R_1$, $R_2$, $R_3$, and $R_4$ are the same as defined above, which process is characterized by subjecting a cholesta-5,7-diene derivative expressed by the following formula (II)

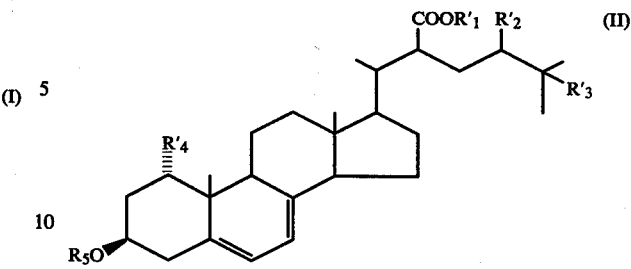

wherein $R'_1$ is a hydrogen atom, alkyl group with 1 to 6 carbon atoms, alkyl group with 1 to 6 carbon atoms having a carboxyl group or amino group, or alkyl group with 1 to 6 carbon atoms having a protected carboxyl group or protected amino group; $R'_2$, $R'_3$ and $R'_4$ independently indicate a hydrogen atom, hydroxyl group, or protected hydroxyl group, and $R_5$ is a hydrogen atom or protecting group; to the thermal isomerization after ultraviolet irradiation in an inert organic medium, followed by deprotection, if necessary.

5. A process for the preparation according to claim 4, wherein $R'_1$ is an alkyl group with 1 to 6 carbon atoms in the aforementioned formula (II).

6. A process for the preparation according to claim 4, wherein $R'_2$, $R'_3$, and $R'_4$ are protected hydroxyl groups and $R_5$ is a protecting group in the aforementioned formula (II).

* * * * *